United States Patent
Sugiyama et al.

(10) Patent No.: US 8,442,282 B2
(45) Date of Patent: May 14, 2013

(54) COMPUTER-AIDED IMAGING DIAGNOSTIC PROCESSING APPARATUS AND COMPUTER-AIDED IMAGING DIAGNOSTIC PROCESSING METHOD

(75) Inventors: Atsuko Sugiyama, Nasushiobara (JP); Hitoshi Yamagata, Otawara (JP); Shigeharu Ohyu, Yaita (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1024 days.

(21) Appl. No.: 11/754,099

(22) Filed: May 25, 2007

(65) Prior Publication Data
US 2007/0274583 A1 Nov. 29, 2007

(30) Foreign Application Priority Data

May 29, 2006 (JP) ................................. 2006-148108

(51) Int. Cl.
*G06K 9/00* (2006.01)
*G06T 15/00* (2006.01)
*G06T 15/40* (2011.01)
*G06T 15/80* (2006.01)

(52) U.S. Cl.
USPC ........... 382/128; 382/130; 382/131; 382/132; 382/168; 382/173; 382/190; 382/254; 382/274; 382/282; 345/419

(58) Field of Classification Search ................. 382/128, 382/130, 131, 132, 168, 173, 190, 254, 274, 382/282; 345/419
See application file for complete search history.

(56) References Cited

U.S. PATENT DOCUMENTS

| | | | |
|---|---|---|---|
| 5,381,518 A * | 1/1995 | Drebin et al. ................. | 345/424 |
| 6,658,080 B1 * | 12/2003 | Poole et al. ....................... | 378/4 |
| 6,690,371 B1 * | 2/2004 | Okerlund et al. ............. | 345/424 |
| 7,277,577 B2 * | 10/2007 | Ying et al. ..................... | 382/168 |
| 7,532,214 B2 * | 5/2009 | Lundstrom .................... | 345/424 |
| 7,660,461 B2 * | 2/2010 | Lundstrom et al. ............ | 382/168 |
| 2002/0183606 A1 * | 12/2002 | Boehler et al. ................ | 600/407 |
| 2004/0179010 A1 * | 9/2004 | Wittenbrink et al. ......... | 345/440 |

(Continued)

FOREIGN PATENT DOCUMENTS

| | | |
|---|---|---|
| JP | 10-127622 | 5/1998 |
| JP | 2001-351120 | 12/2001 |

(Continued)

OTHER PUBLICATIONS

Chang et al. "An automatic method for estimating noise-induced signal variance in magnitude-reconstructed magnetic resonance images." Medical Imaging 2005: Image Processing: Proceedings of the SPIE. 5747. (2005): 1136-1142. Print.*

(Continued)

*Primary Examiner* — Michael A Newman
(74) *Attorney, Agent, or Firm* — Oblon, Spivak, McClelland, Maier & Neustadt, L.L.P.

(57) ABSTRACT

In consideration of the fact that a lung field varies in the density of sponge-like tissue depending on an individual or display region, an opacity curve which gives priority to a nodule candidate region or an extended nodule candidate region can be set by generating a histogram concerning a volume of interest which includes a foreground region, and using the statistical analysis result on the histogram as an objective index.

18 Claims, 22 Drawing Sheets

U.S. PATENT DOCUMENTS

| | | | |
|---|---|---|---|
| 2004/0259065 A1* | 12/2004 | Geiger | 434/272 |
| 2005/0017972 A1* | 1/2005 | Poole et al. | 345/424 |
| 2007/0064982 A1* | 3/2007 | Licato et al. | 382/128 |

FOREIGN PATENT DOCUMENTS

| | | |
|---|---|---|
| JP | 2002-150311 | 5/2002 |
| JP | 2004-57411 | 2/2004 |
| JP | 2005-143733 | 6/2005 |
| WO | WO 2004/102458 | 11/2004 |
| WO | WO 2006/048796 A1 | 5/2006 |

OTHER PUBLICATIONS

Calhoun, et al. "Three-dimensional Volume Rendering of Spiral CT Data: Theory and Method." RadioGraphics. 19. (1999): 745-764. Print.*

U.S. Appl. No. 12/618,968, filed Nov. 16, 2009, Yamagata.

U.S. Appl. No. 11/736,865, filed Apr. 18, 2007, Sumiaki Matsumoto, et al.

John Pawasauskas, "Volume Visualization With Ray Casting", CS563—Advanced Topics in Computer Graphics, Feb. 18, 1997, pp. 1-14.

Gordon Kindlmann, et al. "Semi-automatic generation of transfer functions for direct volume rendering" Volume Visualization, 1998. IEEE Symposium on Research Triangle Park, NC, USA Oct. 19-20, 1998, New York, NY, USA, IEEE, US, Oct. 19, 1998, pp. 79-86, 170, XP010313221 ISBN: 0-8186-9180-8, p. 6, line 1—p. 8, line 27.

Walter Hillen and Felix Fischer: "ExploreDicom Benutzer-Handbuch" 2004, Walter Hillen and Felix Fischer, XP002446568, pp. 25-p. 39.

Jani A. B. et al.: "Opacity Transfer Function Optimization for Volume-rendered Computed Tomography Images of the Prostate", Academic Radiology, Reston, VA, US, vol. 12, No. 6, Jun. 2005, pp. 761-770, XP004922372, ISSN: 1076-6332, the whole document.

Alper Selver et al.: "A software tool for interactive generation, representation, and systematical storage of transfer functions for 3D medical images" Computer Methods and Programs in Biomedicine, Elsevier, Amsterdam, NL, vol. 86, No. 3, May 3, 2007, pp. 270-280, XP022054455, ISSN: 0169-2607.

Japanese Office Action issued Jan. 24, 2012 in patent application No. 2007-142273 with English translation.

* cited by examiner

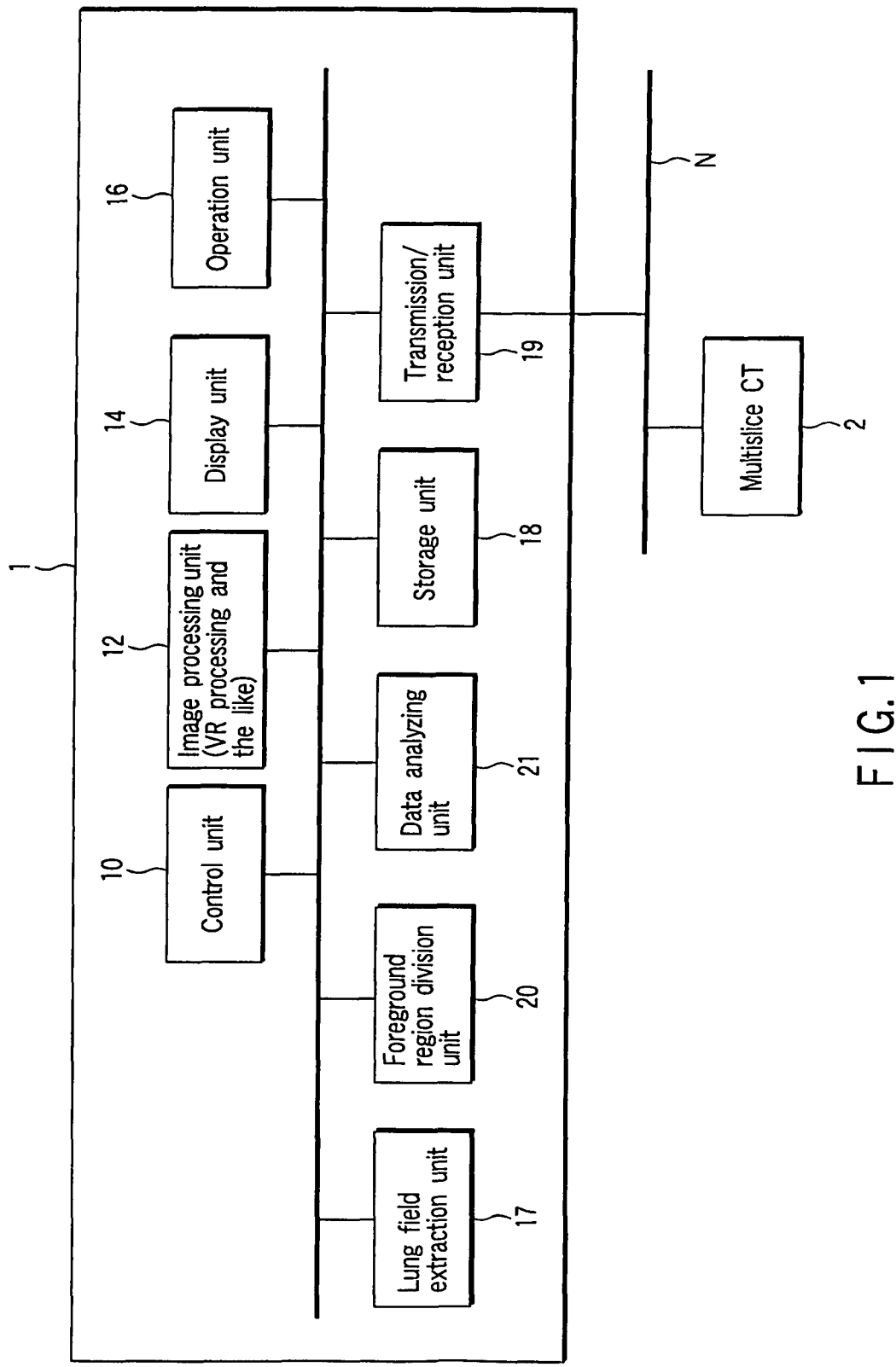
F I G. 1

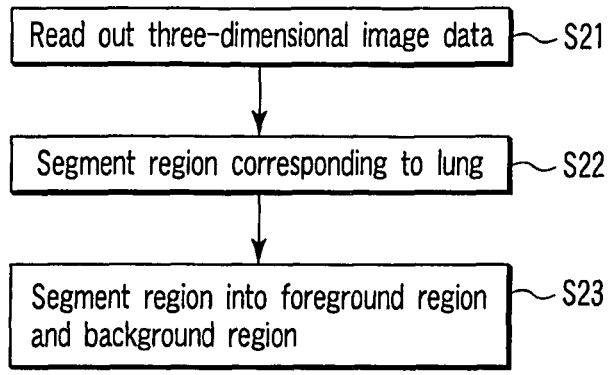
F I G. 3A
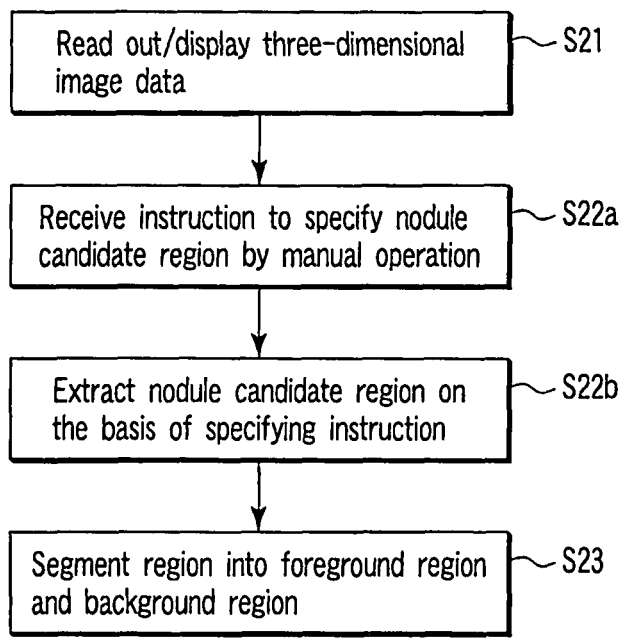
F I G. 3B

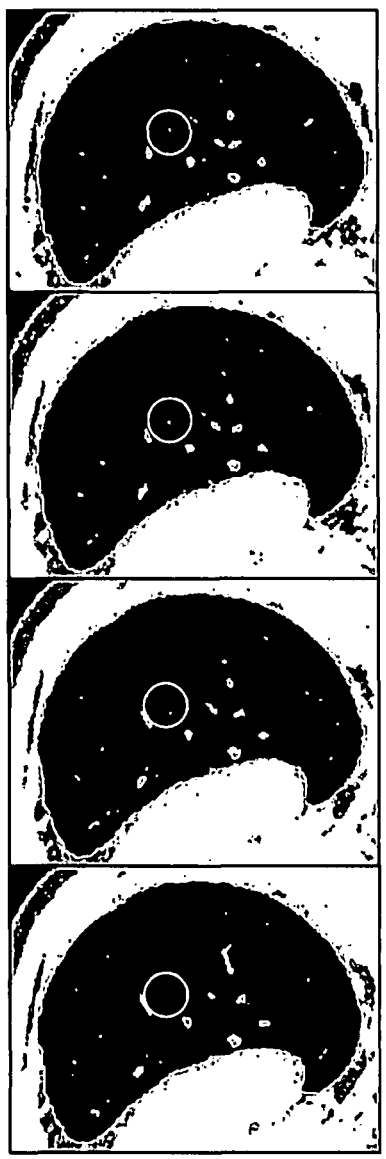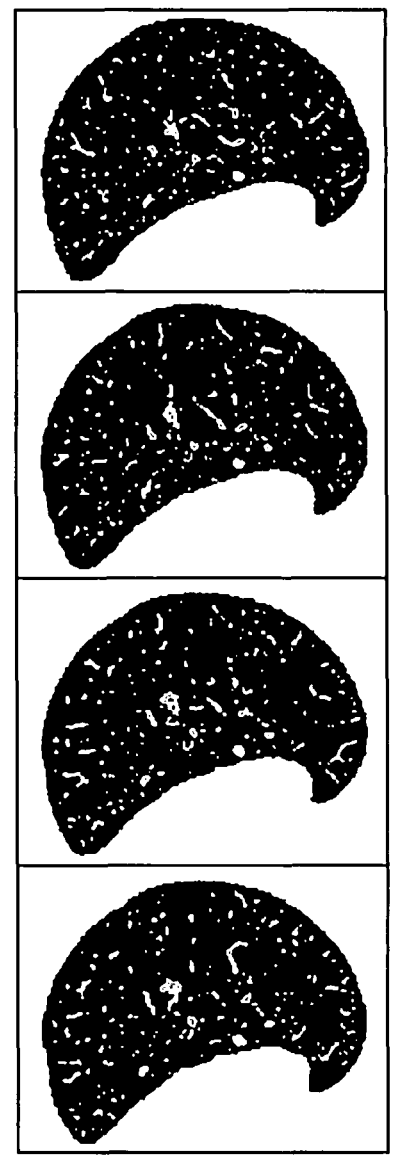
F I G. 4A
F I G. 4B

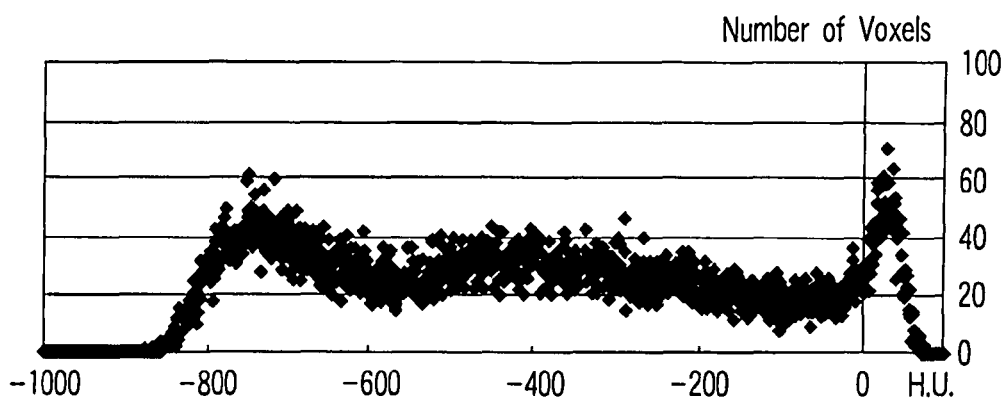
FIG. 9
CT value (reference value)
−1000 : Air
−900 : Lung field (normal)
−750 : Frosted glass shadow
−650 : Fine grained shadow
−550 : Fine branch shadow
50 : Dense infiltrative shadow
FIG. 10
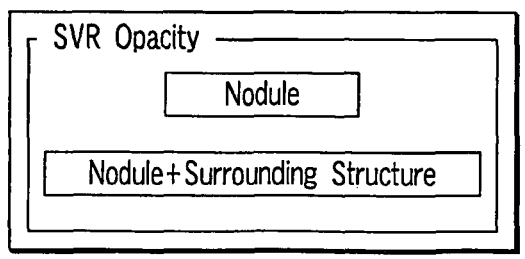
FIG. 11

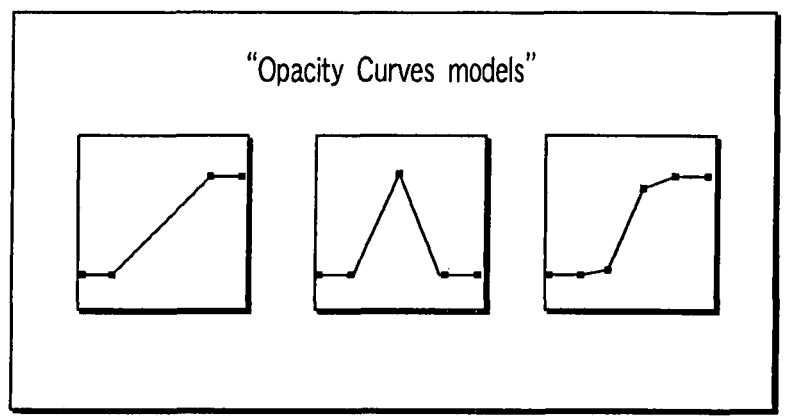
F I G. 19
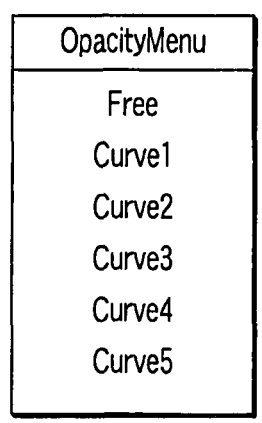
F I G. 20

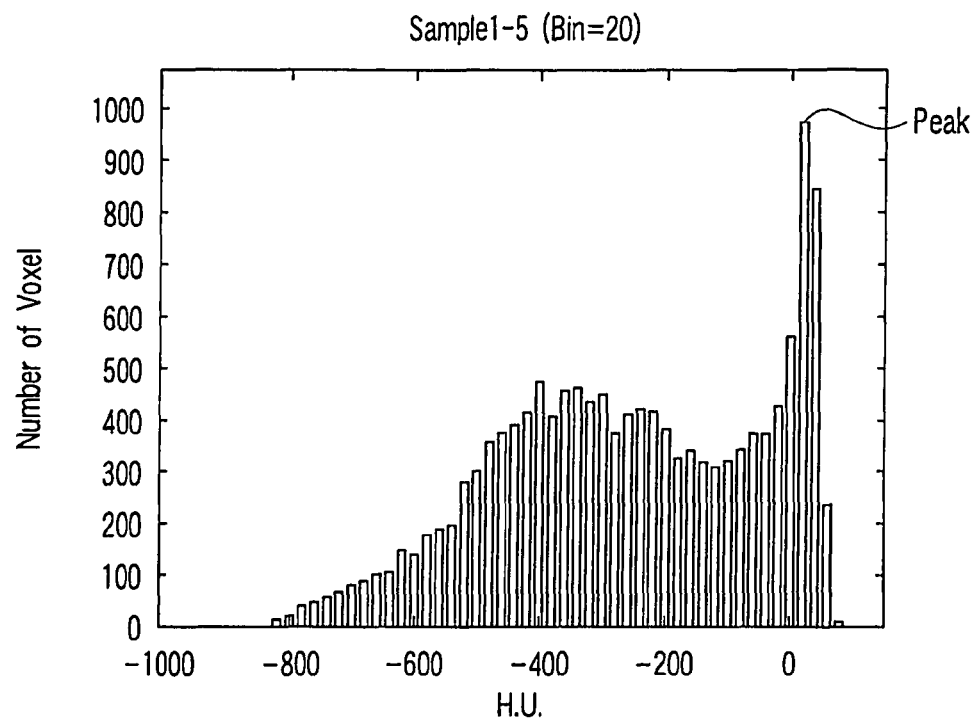
F I G. 34
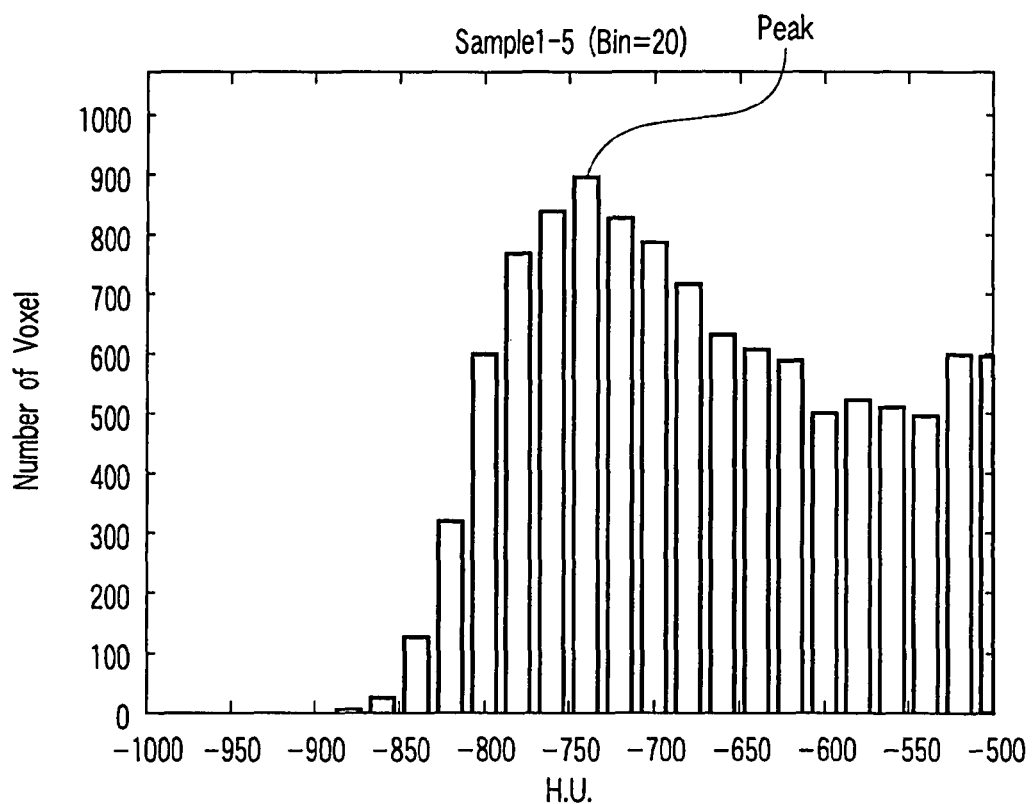
F I G. 35

COMPUTER-AIDED IMAGING DIAGNOSTIC PROCESSING APPARATUS AND COMPUTER-AIDED IMAGING DIAGNOSTIC PROCESSING METHOD

CROSS-REFERENCE TO RELATED APPLICATIONS

This application is based upon and claims the benefit of priority from prior Japanese Patent Application No. 2006-148108, filed May 29, 2006, the entire contents of which are incorporated herein by reference.

BACKGROUND OF THE INVENTION

1. Field of the Invention

The present invention relates to a computer-aided imaging diagnostic processing apparatus and computer-aided imaging diagnostic processing method which can satisfactorily visualize a desired target by properly setting parameters in volume rendering (VR) processing.

2. Description of the Related Art

Currently, in Japan, lung cancer has become the first cause of malignant tumor death and has increased steadily. This leads to strong social demands for not only prevention by anti-smoking measures but also early detection. In Japan, each municipality has practiced lung cancer screening by plain chest radiograph and sputum cytology. A 1998 report by "Study Group Concerning Cancer Screening Effectiveness Evaluation" of the Ministry of Health and Welfare concluded that current lung cancer screening had little effect if any. X-ray computed tomography (CT) can detect a lung field type lung cancer more easily than a plain chest radiograph. However, this technique could not be used for screening because it took a long imaging time before the advent of a helical scan type CT in 1990. Shortly after the advent of helical CT, a method of imaging at a relatively low X-ray tube current (to be referred to as low-dose helical CT hereinafter) has been developed to reduce exposure to radiation, and pilot studies have been made on lung cancer screening using this technique in Japan and the U.S. The study results have demonstrated that low-dose helical CT has a higher lung cancer detection rate than plain chest radiograph.

An increase in the number of CT detector rows after 1998 has shortened the time required for helical CT imaging. The latest multi-detector helical CT, such as 64 rows model, can image the entire lungs with an almost isotropic resolution of less than 1 mm in less than 10 sec. Technical innovation of CT raises the possibility that it can detect smaller lung cancers. However, the multi-detector helical CT generates roughly thousand images per scan, and hence the load required for interpretation of radiograms greatly increases.

When a volume rendering image of a lung field is to be displayed by using a conventional computer-aided imaging diagnostic processing apparatus, the apparatus uses a constant lung field opacity curve (opacity characteristic curve) regardless of density differences in the lung field or individual density differences in the lung field. In order to obtain a desired volume rendering image, therefore, the user adjusts parameters (an opacity curve and the like) for each volume rendering operation by using an imaging display apparatus user interface.

In volume rendering display of a CT lung field, it is necessary to obtain feature amounts of a volume of interest (VOI) to be displayed and determine parameters for volume rendering display on the basis of these feature amounts. It is, however, difficult to obtain a volume rendering image desired by the user by using these feature amounts, and hence it has required a very long time to adjust parameters by using an imaging display apparatus user interface. This increases the load on a doctor who interprets radiograms. For this reason, this technique is rarely used for diagnosis. That is, volume rendering image generation corresponding to each purpose is rarely used for diagnosis because it further increases the load on the doctor who interprets radiograms in spite of the fact that it can generate isotropic three-dimensional image data.

Under the circumstances, in order to establish low-dose helical CT as a lung cancer screening method and allow the use of volume rendering images for imaging diagnosis, demands have arisen for a method of easily displaying volume rendering images corresponding to purposes.

BRIEF SUMMARY OF THE INVENTION

The present invention has been made in consideration of the above situation, and has as its object to provide a computer-aided imaging diagnostic processing apparatus and computer-aided imaging diagnostic processing method which can set image generation parameters which allow proper visualization of a target automatically or with minimum operation.

According to an aspect of the present invention, it is provided that a medical image processing apparatus which generates an image on the basis of data acquired by using a medical imaging device comprises a region specifying unit which specifies a processing target region in an image, a parameter setting unit which executes statistical processing concerning an image in the processing target region and sets an image generation parameter on the basis of the statistical result, and an image generating unit which generates a projection image on the basis of the set image generation parameter.

According to another aspect of the present invention, it is provided that a medical image processing method comprising specifying a processing target region in an image acquired by using a medical imaging device, executing statistical processing concerning an image in the processing target region and setting an image generation parameter on the basis of the statistical result, and generating a projection image on the basis of the set image generation parameter.

BRIEF DESCRIPTION OF THE SEVERAL VIEWS OF THE DRAWING

FIG. 1 is a block diagram showing the arrangement of a computer-aided imaging diagnostic processing apparatus 1 according to this embodiment;

FIGS. 3A and 3B are flowcharts showing a lung field extraction processing procedure;

FIG. 4A is a view showing images represented by the three-dimensional image data acquired by a multislice CT 2, and FIG. 4B is a view showing foreground portion images segmented from the images in FIG. 4A;

FIG. 9 is a graph showing an H.U. histogram concerning a VOI which is an extracted volume of interest;

FIG. 10 is a table showing general CT values (H.U. values);

FIG. 11 is a view showing an example of an input window for selecting a nodule candidate region priority mode or an extended nodule candidate region priority mode;

FIG. 19 is a view showing examples of an opacity curve other than a linear function;

FIG. 20 is a view showing an example of a window for selecting an opacity curve;

FIG. 34 is a graph showing an example of a histogram with a bin width of 20 in a case wherein the nodule candidate region priority mode is selected;

FIG. 35 is a graph showing an example of a histogram with a bin width of 20 in a case wherein the extended nodule candidate region priority mode is selected;

DETAILED DESCRIPTION OF THE INVENTION

Figure 2A:
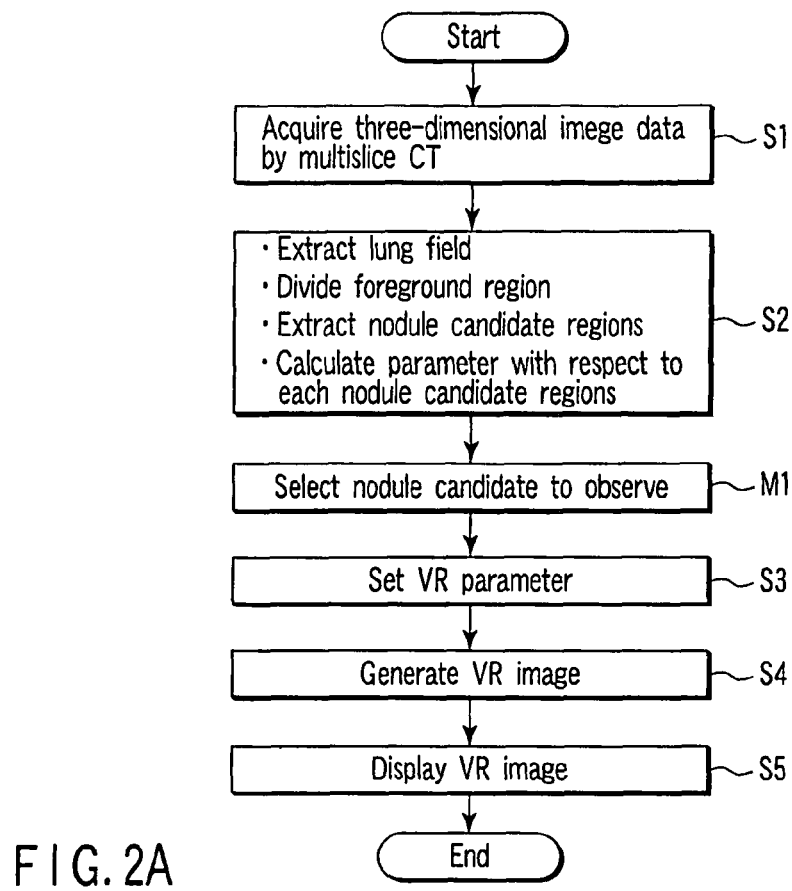
FIG. 2A is a flowchart showing a processing procedure including the computer-aided imaging diagnostic processing.

The first and second embodiments of the present invention will be described below with reference to the views of the accompanying drawing. Note that in the following description, the same reference numerals denote constituent elements having almost the same functions and arrangements, and a repetitive description will be made only when required.

For the sake of a concrete description, each embodiment will exemplify a case wherein a lung field is a diagnosis target. However, the present invention is not limited to this, and the technical idea of each embodiment can be applied to a case wherein, for example, a breast or liver is a diagnosis target.

First Embodiment

FIG. 1 is a block diagram showing the arrangement of a computer-aided imaging diagnostic processing apparatus 1 according to this embodiment. Referring to FIG. 1, the computer-aided imaging diagnostic processing apparatus 1 comprises a control unit 10, image processing unit 12, display unit 14, operation unit 16, storage unit 18, transmission/reception unit 19, lung field extraction unit 17, foreground region division unit 20, and data analyzing unit 21.

The computer-aided imaging diagnostic processing apparatus according to this embodiment can use, for example, a general-purpose computer apparatus as basic hardware. The lung field extraction unit 17 and the data analyzing unit 21 can be implemented by causing a processor mounted in the above computer apparatus to execute imaging diagnostic processing programs. In this case, it suffices to implement the computer-aided imaging diagnostic processing apparatus 1 by installing the above imaging diagnostic processing programs in the above computer apparatus in advance or by distributing the above imaging diagnostic processing programs upon recording them on a removable recording medium such as a magnetic disk, magnetooptic disk, optical disk, or semiconductor memory or through a network, and installing the programs in the above computer apparatus as needed. Note that some or all of the above units can be implemented by hardware such as logic circuits. In addition, each of the above units can be implemented by a combination of hardware and software control.

The control unit 10 dynamically or statically controls the respective units constituting the computer-aided imaging diagnostic processing apparatus. The control unit 10 comprehensively controls the lung field extraction unit 17, the data analyzing unit 21, and the like in lung field extraction and VR parameter setting, in particular.

The image processing unit 12 performs predetermined image processing corresponding to diagnosis purposes by using the images acquired by various kinds of medical imaging devices. The image processing unit 12 executes VR processing in accordance with the opacity curve set by a VR parameter setting function, in particular. Performing image processing by using the image processing unit 12 will generate an image (diagnostic image) used for imaging diagnosis.

The display unit 14 displays an input window for setting/selecting/changing a histogram and opacity curve concerning a predetermined image and a predetermined region, an input window for performing other operations, and the like in a predetermined form.

The operation unit 16 includes a trackball, various switches, a mouse, a keyboard, and the like for inputting various instructions, conditions, and the like from the operator to the apparatus 1. The operation unit 16 also includes a predetermined interface for setting/selecting/changing an opacity curve and the like in VR parameter setting operation to be described later.

The lung field extraction unit 17 implements the lung field extraction function under the control of the control unit 10. The processing implemented by this lung field extraction function will be referred to as lung field extraction function.

The storage unit 18 stores patient data, image data acquired by various kinds of medical imaging devices typified by a multislice CT 2, programs for executing processing based on the lung field extraction function, various kinds of image processing typified by VR processing, and the like, and a dedicated program for implementing a VR parameter setting function.

The transmission/reception unit 19 transmits/receives information which can be used for diagnosis to/from another apparatus or a database through a network.

The foreground region division unit 20 extracts a lung field by executing predetermined image processing using the three-dimensional image data acquired by the X-ray CT apparatus, and segments the extracted lung field into a foreground region (a region almost corresponding to lung blood vessels and a nodule) and a background region (a region other than the foreground region).

The data analyzing unit 21 implements the VR parameter setting function. This function extracts a region (nodule candidate region) which can be a nodule and a region (extended nodule candidate region) comprising a nodule candidate region and a surrounding region continuous with it by using an image (region segmented image) segmented into a foreground region and a background region by lung field extraction processing, and performs statistical analysis using a histogram concerning the H.U. (Hounsfield Unit) values of these regions, thereby determining a VR parameter (i.e., an opacity curve). The processing implemented by this VR parameter setting function will be referred to as VR parameter setting processing.

The operation of the computer-aided imaging diagnostic processing apparatus 1 having the above arrangement will be described next.

Figure 2B:
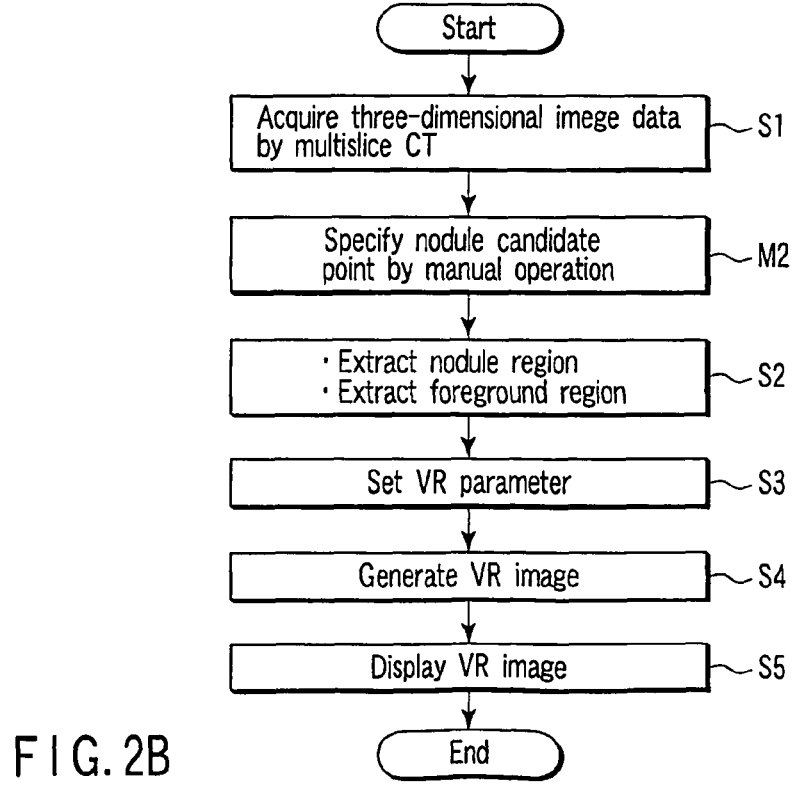
FIG. 2B is a flowchart showing a processing procedure including manual operation.

FIG. 2 is a flowchart showing a processing procedure in a case wherein the computer-aided imaging diagnostic processing apparatus 1 performs volume rendering image generation/display. As shown in FIG. 2A and FIG. 2B, in this volume rendering image generation/display, the computer-aided imaging diagnostic processing apparatus 1 performs processes, e.g., acquisition of three-dimensional image data by the multislice CT 2, lung field extraction, VR parameter setting, VR rendering image generation, and VR image display. The contents of each process will be described below.

(Acquisition of X-ray CT Three-dimensional Image Data: Step S1)

The multislice CT 2 images the entire chest portion including the lungs of a subject as a diagnosis target, and performs predetermined image reconstruction and the like, thereby acquiring three-dimensional image data. Note that the imaging method (e.g., a conventional scan method or helical scan method) to be used and the image reconstruction method to be used are not specifically limited. The storage unit 18 of the computer-aided imaging diagnostic processing apparatus 1 stores the acquired three-dimensional image data by network communication or through a portable external medium or the like.

(Lung Field Extraction Processing: Step S2)

FIG. 3A is a flowchart showing a lung field extraction processing procedure. As shown in FIG. 3A, first of all, the lung field extraction unit 17 reads the three-dimensional image data acquired by, for example, the multislice CT from the storage unit 18 (step S21). The lung field extraction unit 17 then segments a region corresponding to the lungs from the above three-dimensional image data (step S22). This processing can use an existing method (Hu S., Hoffman E. A., Reinhardt J. M., "Automatic lung segmentation for accurate quantitation of volumetric X-ray CT images", IEEE Trans Med Imaging 2001; 20: 490-498).

The lung field extraction unit 17 then segments the lung region obtained in step S22 into a foreground region almost corresponding to lung blood vessels and a nodule and a background region other than the foreground region (step S23). This processing can use, for example, existing adaptive threshold processing (Manay S., Yezzi A., "Antigeometric diffusion for adaptive thresholding and fast segmentation", IEEE Trans Image Processing 2003; 12: 1310-1323). FIG. 4A is a view showing images using the three-dimensional image data acquired by the multislice CT 2. FIG. 4B is a view showing images of the foreground region segmented from the image data shown in FIG. 4A. A nodule exists in each circle in FIG. 4A. Referring to FIG. 4B, each black range corresponds to a lung region, and a hollow region in the lung region represents a lung region foreground portion. Then the nodule which user wants to observe is selected.

Note that this lung field extraction processing can also be implemented by, for example, specifying a nodule candidate region by manual operation through the operation unit 16 (step M1 shown in FIG. 2B).

FIG. 3B is a flowchart showing a lung field extraction processing procedure including manual operation. As shown in FIG. 3B, first of all, the lung field extraction unit 17 reads three-dimensional image data from the storage unit 18. The display unit 14 displays a three-dimensional image based on the read data (step S21). When the operator specifies a nodule candidate region on the displayed three-dimensional image by manual operation using the operation unit 16, the control unit 10 receives the specifying instruction (step S22*a*). The lung field extraction unit 17 extracts a nodule candidate region from the three-dimensional image data on the basis of the specified nodule candidate region (step S22*b*), and segments the extracted nodule candidate region into a foreground region and a background region (step S23).

(VR Parameter Setting Function: Step S3)

Figure 5:
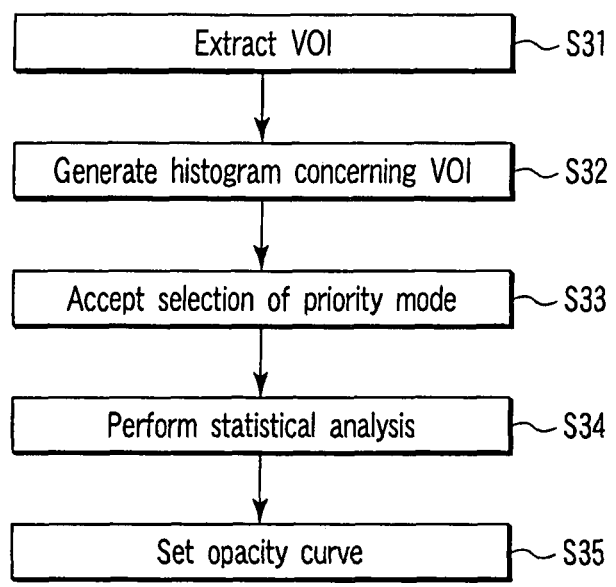
FIG. 5 is a flowchart showing a VR parameter setting processing procedure.
Figure 6A:
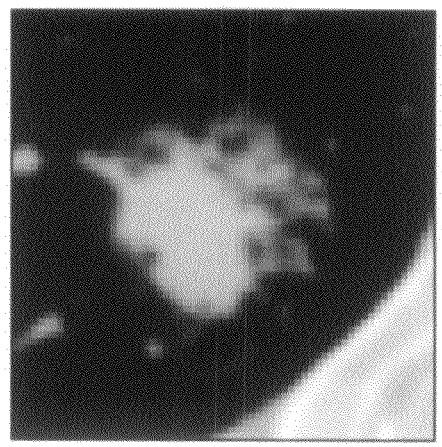
FIGS. 6A, 6B, and 6C are views each showing an example of a VOI which is an extracted volume of interest.
Figure 6B:
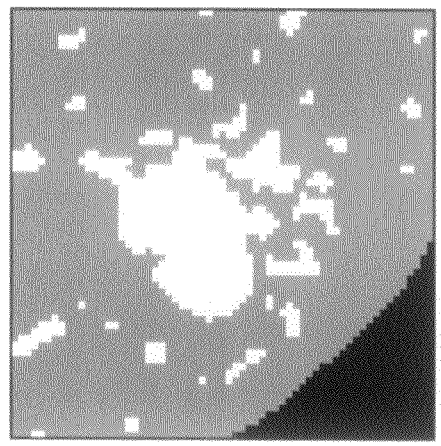
Figure 6C:
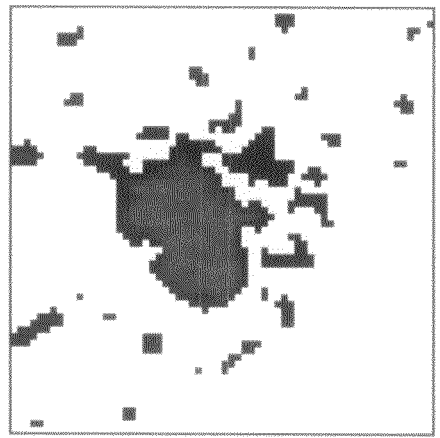
Figure 7:
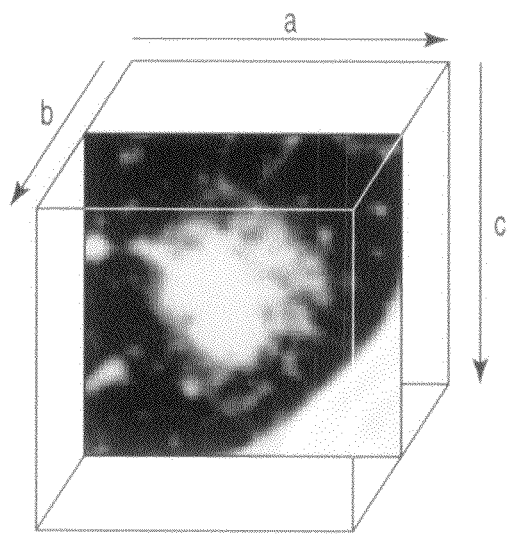
FIG. 7 is a view showing an example of a VOI extracted in step S31.
Figure 8:
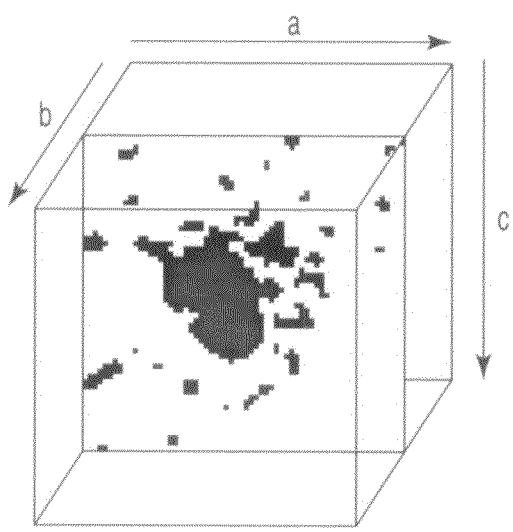
FIG. 8 is a view showing a foreground region of a VOI extracted in step S31.

FIG. 5 is a flowchart showing a VR parameter setting processing procedure. As shown in FIG. 5, the data analyzing unit 21 determines the center and size of the VOI of a rectangular parallelepiped region in the region segmented image generated in step S23 by using ellipse information obtained by the technique disclosed in Jpn. Pat. Appln. KOKAI Publication No. 2006-239005. FIG. 6A shows a cross-section of the VOI in FIG. 4A. FIG. 6B shows a cross-section of the VOI in FIG. 4B. FIG. 6C shows a foreground extraction cross-section using the cross-section in FIG. 4B. FIGS. 7 and 8 show VOIs extracted in step S31.

The data analyzing unit 21 then generates a histogram of H.U. values concerning the extracted VOI which includes the only foreground region, as shown in, for example, FIG. 9 (step S32). Note that FIG. 10 shows general CT values (i.e., H.U. values).

The data analyzing unit 21 then accepts the selection of a nodule candidate region priority mode or an extended nodule candidate region priority mode (step S33). In this case, the nodule candidate region priority mode is a mode of setting an opacity curve for preferentially visualizing a nodule candidate region. The extended nodule candidate region priority mode is a mode of setting an opacity curve for preferentially visualizing an extended nodule candidate region. In the mode selection in this step, it is preferable to accept selecting operation performed by a dedicated switch provided for the operation unit 16 or through an input window shown in FIG. 11. Selecting the nodule candidate region priority mode or the extended nodule candidate region priority mode determines whether to preferentially visualize a nodule candidate region or an extended nodule candidate region. For this reason, selecting the nodule candidate region priority mode or the extended nodule candidate region priority mode amounts to selecting an image type.

The data analyzing unit 21 then executes statistical analysis corresponding to the mode selected in step S33 by using an H.U. histogram concerning a generated VOI (step S34). Statistical analysis executed in this case is to acquire the average, standard deviation, variance, and the like of the histogram by performing fitting processing for the histogram using a probability density function.

Figure 14:
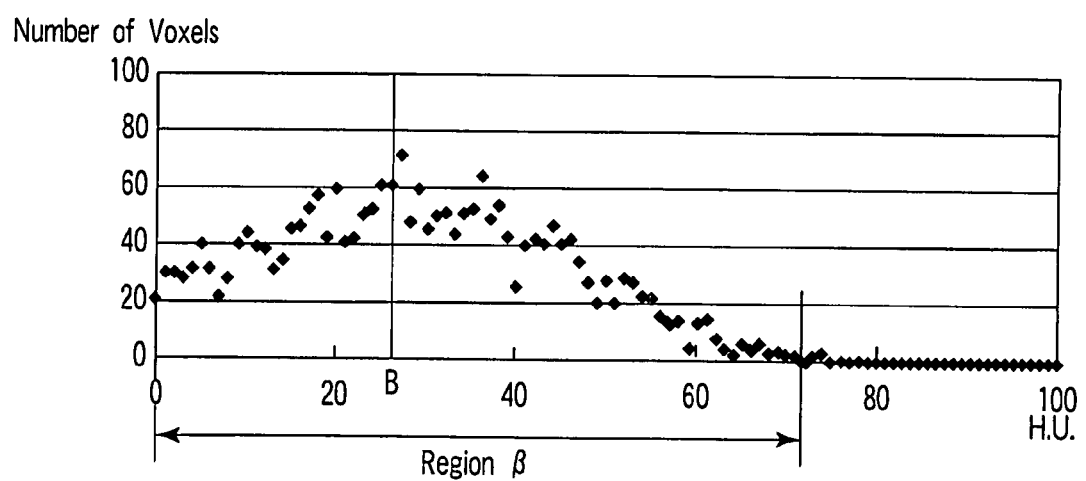
FIG. 14 is a graph for explaining statistical analysis executed in VR parameter setting processing in nodule candidate region priority mode.
Figure 15:
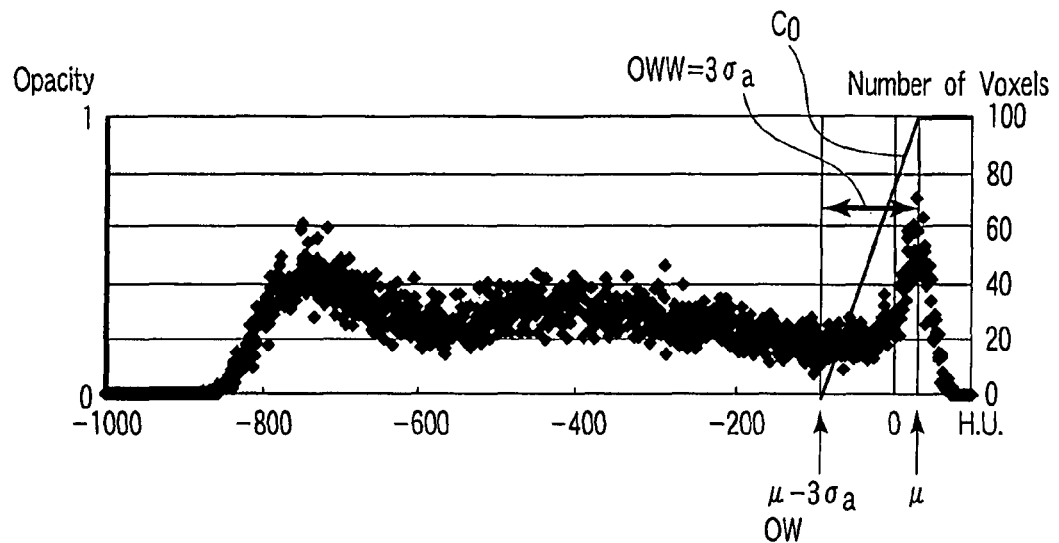
FIG. 15 is a graph for explaining an opacity curve set by VR parameter setting processing in the nodule candidate region priority mode.

That is, when the nodule candidate region priority mode is selected, the data analyzing unit 21 sets, as a value A, the H.U. value which is maximized in a positive region on the histogram, and sets, as a region α, a region ranging from a position corresponding to H.U.=0 to a position corresponding to a total voxel count of 0 through a position corresponding to H.U.=B, as shown in FIG. 14 and FIG. 15. In addition, the data analyzing unit 21 performs statistical analysis of estimating a Gaussian distribution function by performing fitting calculation using the probability density function (plotted in FIG. 15) based on equation (1) given below:

$$f(x) = Ae^{\frac{-(x-\mu_a)^2}{\sigma_a^2}} \quad (1)$$

where $\mu_a$ is an average, $\sigma_a$ is a standard deviation, and $\sigma_a^2$ is a variance.

Figure 12:
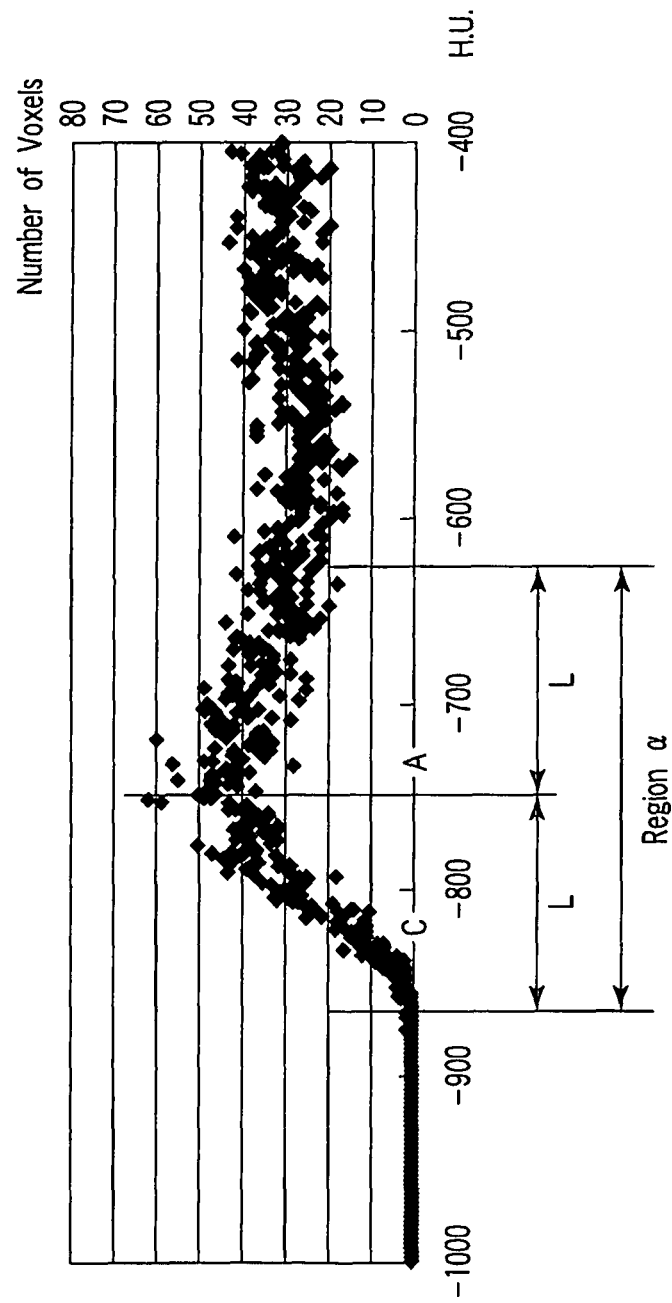
FIG. 12 is a graph for explaining statistical analysis executed in VR parameter setting processing in extended nodule candidate region priority mode.
Figure 13:
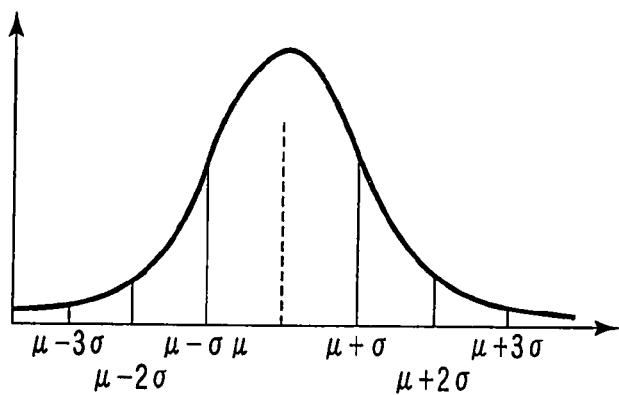
FIG. 13 is a graph of a general probability density function.
Figure 16:
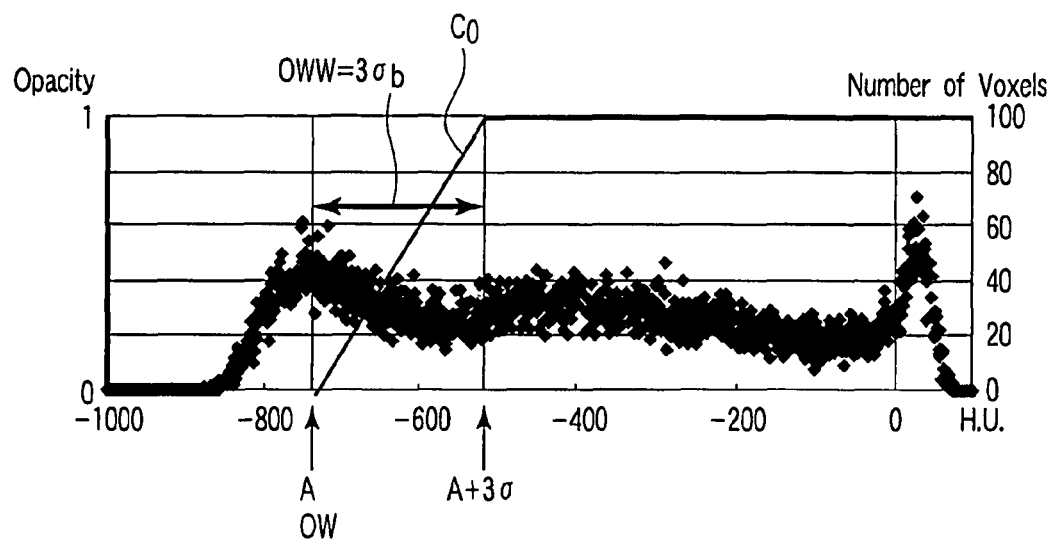
FIG. 16 is a graph for explaining an opacity curve set by VR parameter setting processing in the extended nodule candidate region priority mode.

When the extended nodule candidate region priority mode is selected, the data analyzing unit 21 sets, as a value B and a value C, respectively, the H.U. value which is maximized in a negative region and the H.U. value which makes the total voxel count become 0 when H.U.=A or less, and sets L=|A−C|, as shown in FIG. 12 and FIG. 16. As shown in FIG. 14, the data analyzing unit 21 performs statistical analysis of estimating a Gaussian distribution function by performing fitting calculation using the probability density function (see FIG. 16) based on equation (2) given below with respect to a region β ranging from C to 2 L:

$$f(x) = Ae^{\frac{-(x-\mu_b)^2}{\sigma_b^2}} \quad (2)$$

where $\mu_b$ is an average, $\sigma_b$ is a standard deviation, and $\sigma_b^2$ is a variance.

The data analyzing unit 21 then sets an opacity curve by determining an opacity window level (OWL) and an opacity window width (OWW) using the statistical analysis result (step S34). That is, when the nodule candidate region priority mode is selected, the data analyzing unit 21 sets an opacity curve Co shown in FIG. 15 as OWL=$\mu_a$−3$\sigma_a$ and OWW=3$\sigma_a$. When the extended nodule candidate region priority mode is selected, the data analyzing unit 21 sets an opacity curve Co shown in FIG. 16 as OWL=OWW=3$\sigma_b$.

Note that the above determined values of OWL and OWW are examples, and other arbitrary real numbers can be selected as needed.

In addition, it suffices to obtain an opacity curve characteristic such that the value of opacity changes with a change in voxel value from the opacity value at the lowest voxel value in the window to the opacity value at the highest voxel value in the window. It suffices to linearly change the value of opacity or change it in accordance with the curve obtained by using a predetermined curve function within this interval.

(VR Rendering Image Generation Processing: Step S4)

VR processing is executed by using the VR parameter calculated in step S3, thereby generating a VR image. This processing can use the technique disclosed in John Pawasauskas, "Volume Visualization With Ray Casting", CS563-Advanced Topics in Computer Graphics, Feb. 18, 1997.

(VR Image Display Processing: Step S5)

The display unit 14 displays the VR image generated in step S4 in a predetermined form. That is, when preferentially displaying a nodule candidate region, the display unit 14 displays the VR image generated in accordance with the opacity curve shown in FIG. 15 (see FIG. 17). When preferentially displaying an extended nodule candidate region, the display unit 14 displays the VR image generated in accordance with the opacity curve shown in FIG. 16 (see FIG. 18).

Figure 17:
FIG. 17 is a view showing an example of a VR image obtained in accordance with VR parameters set in the nodule candidate region priority mode.
Figure 18:
FIG. 18 is a view showing an example of a VR image obtained in accordance with VR parameters set in the extended nodule candidate region priority mode.
Figure 21:
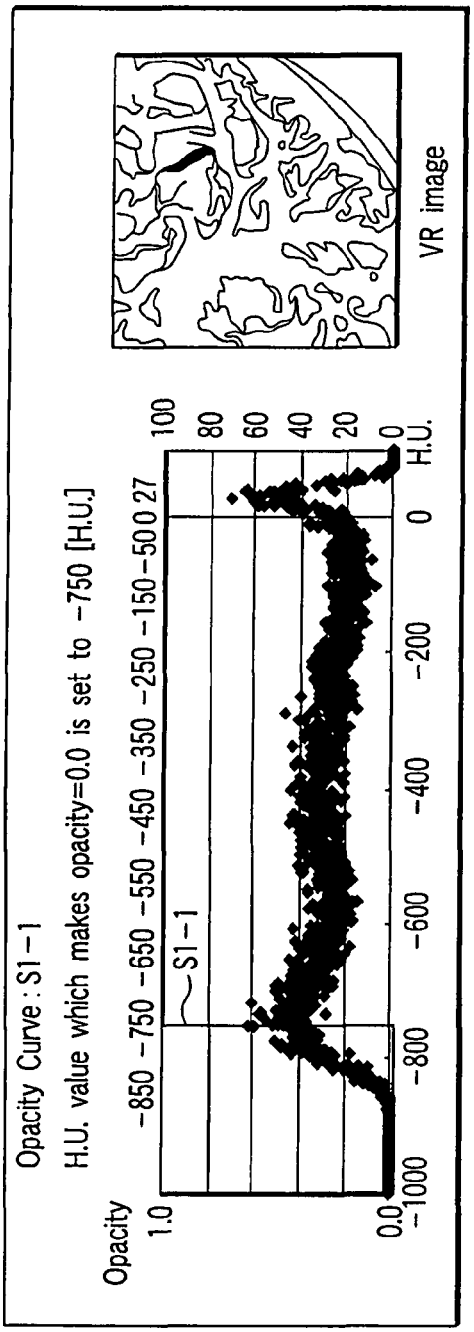
FIG. 21 is a graph showing an opacity curve with a gradient S1-1 and an H.U. value of −750 [H.U.] which makes opacity=0.0.
Figure 22:
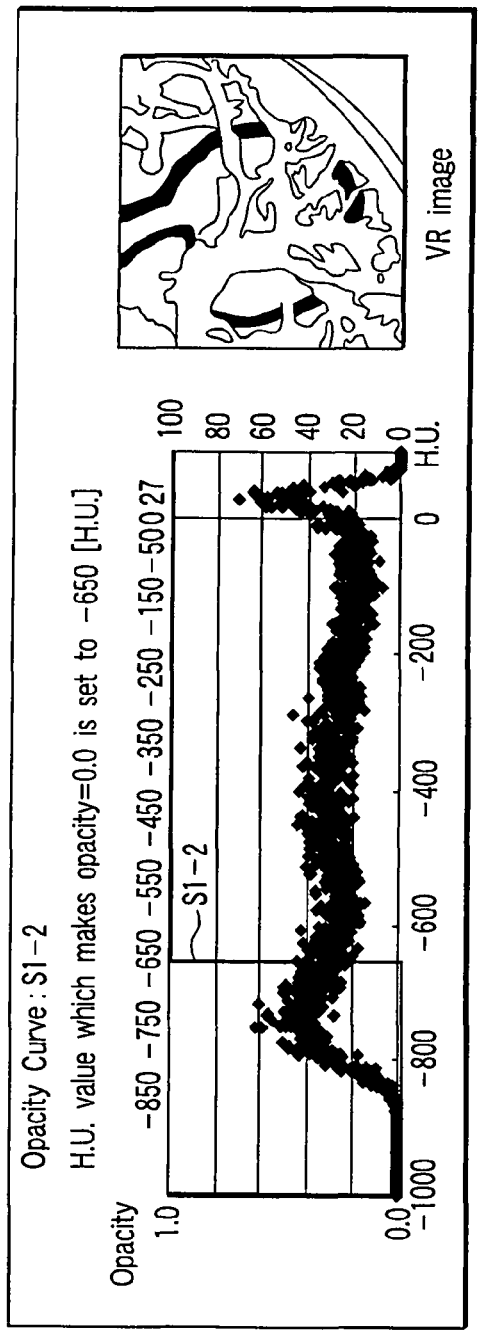
FIG. 22 is a graph showing an opacity curve with the gradient S1-1 and an H.U. value of −650 [H.U.] which makes opacity=0.0.

Note that the display unit 14 may simultaneously display the opacity curve and VR image obtained by VR parameter setting (i.e., the opacity curve shown in FIG. 15 [or FIG. 16] and the VR image or the VR image of the foreground region shown in FIG. 17 [or FIG. 18]).

(First Modification)

The above embodiment has exemplified the case wherein an opacity curve which is a linear function is set as a typical example. However, an opacity curve can be defined by a desired function or curve sketching instead of a linear function. FIG. 19 shows another typical example of the opacity curve. It is preferable from the viewpoint of operability that a desired one of preset opacity curves can be selected by using a user interface like that shown in FIG. 20.

(Second Modification)

Performing predetermined operation makes it possible to change the VR parameter (opacity curve) set in accordance with the above embodiment to another setting. The contents of this operation will be described below with reference to a case wherein an opacity curve is a linear function.

An opacity curve as a linear function can be changed in accordance with two condition settings. One setting is the gradient of an opacity curve, and the other setting is the H.U. value which makes opacity=0.

Figure 23:
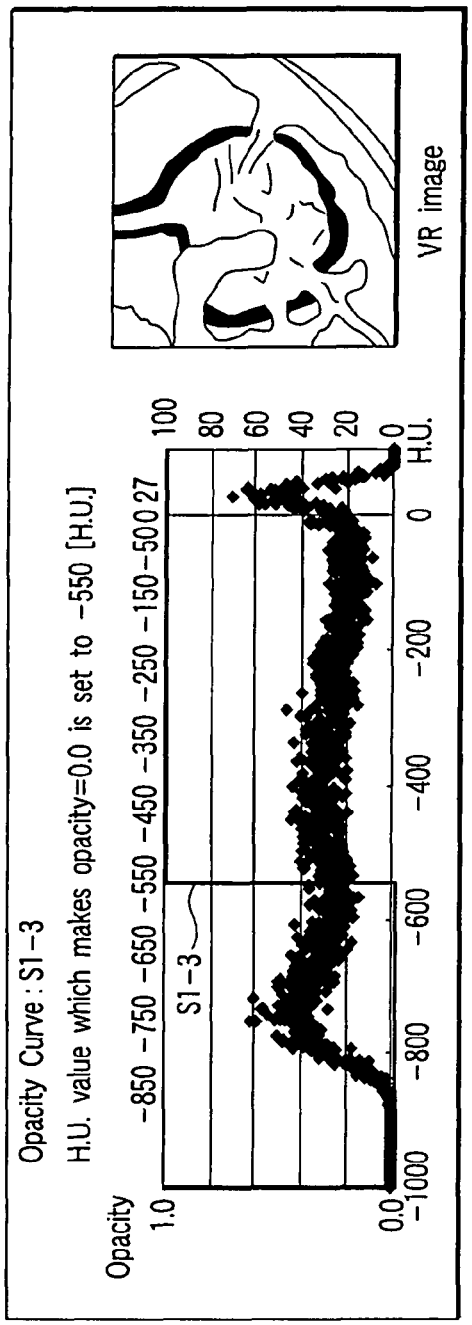
FIG. 23 is a graph showing an opacity curve with the gradient S1-1 and an H.U. value of −550 [H.U.] which makes opacity=0.0.
Figure 24:
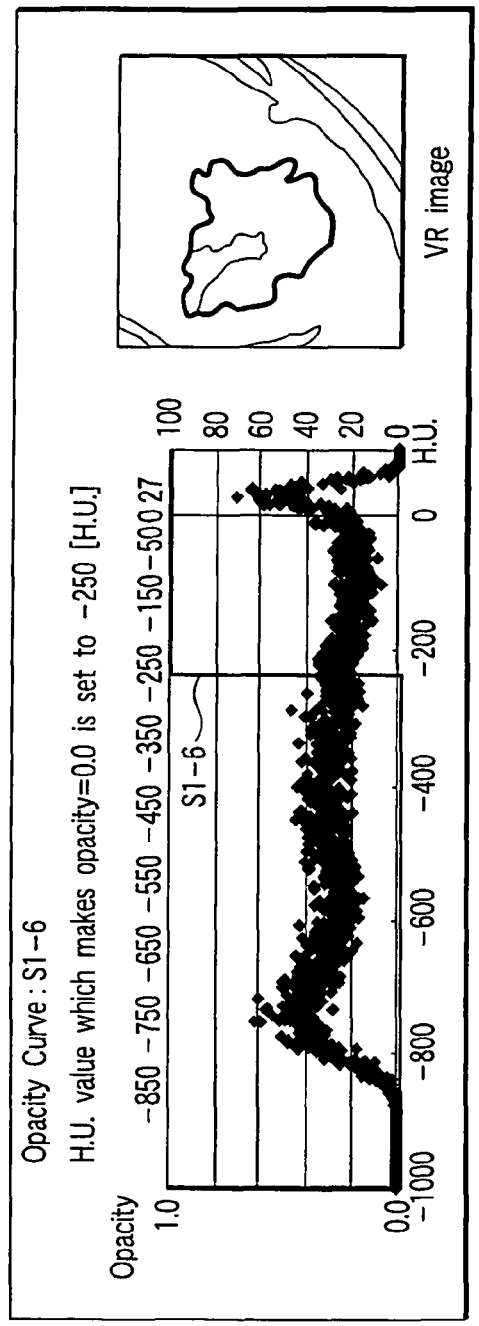
FIG. 24 is a graph showing an opacity curve with the gradient S1-1 and an H.U. value of −250 [H.U.] which makes opacity=0.0.

FIGS. 21 to 24 each show an opacity curve having a gradient S1-1 and the VR image generated by using the opacity curve, which are obtained when the H.U. value which makes opacity=0 is changed every 100 [H.U.] (note, however, that the H.U. value is changed in units of 300 [H.U.] in the cases shown in FIGS. 23 and 24). In the case shown in FIG. 21 (the lower limit of the opacity is −750 [H.U.] with the gradient S1-1), many blood vessels around a nodule are displayed, and hence the nodule is hidden by a surrounding structure. In the case shown in FIG. 22 (the lower limit of the opacity is −650 [H.U.] with the gradient S1-1), the nodule is easily viewable and the relationship between the nodule and the blood vessels is easily comprehensible as compared with the case shown in FIG. 21. In the case shown in FIG. 23 (the lower limit of the opacity is −550 [H.U.] with the gradient S1-1), the nodule is more easily viewable. In the case shown in FIG. 24 (the lower limit of the opacity is −250 [H.U.] with the gradient S1-1), the nodule is visualized, but the blood vessels are hidden.

Figure 25:
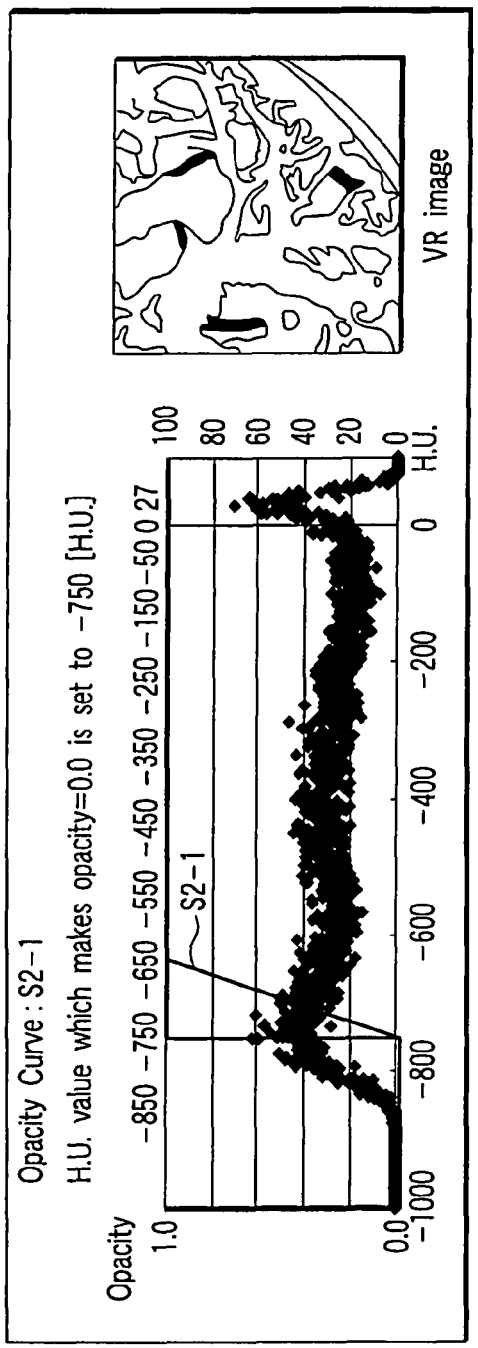
FIG. 25 is a graph showing an opacity curve with a gradient S2-1 and an H.U. value of −750 [H.U.] which makes opacity=0.0.

FIG. 25 shows an opacity curve and the VR image generated by using the opacity curve in a case wherein the lower limit of the opacity is −750 [H.U.] with a gradient S2-1. In this case, the blood vessels surrounding the nodule are visualized so as to be easily viewable.

Figure 26:
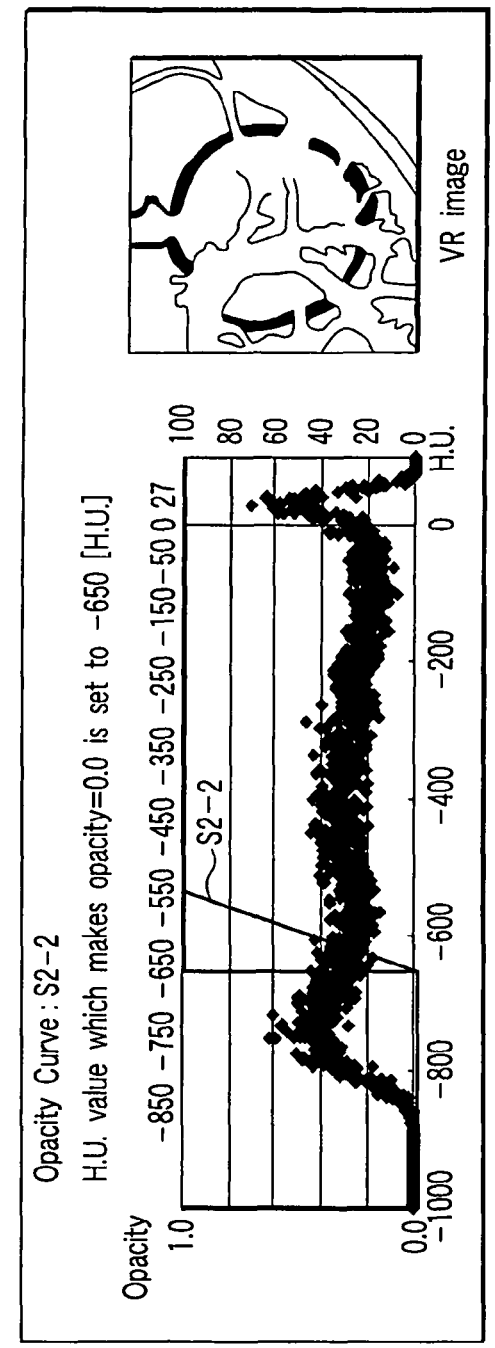
FIG. 26 is a graph showing an opacity curve with the gradient S2-1 and an H.U. value of −650 [H.U.] which makes opacity=0.0.

FIG. 26 shows an opacity curve and the VR image generated by using the opacity curve in a case wherein the lower limit of the opacity is −650 [H.U.] with the gradient S2-1. In this case, the blood vessels surrounding the nodule which are displayed reduce in number as compared with the case shown in FIG. 25, and the nodule and the relationship between the nodule and the blood vessels are easily viewable.

Figure 27:
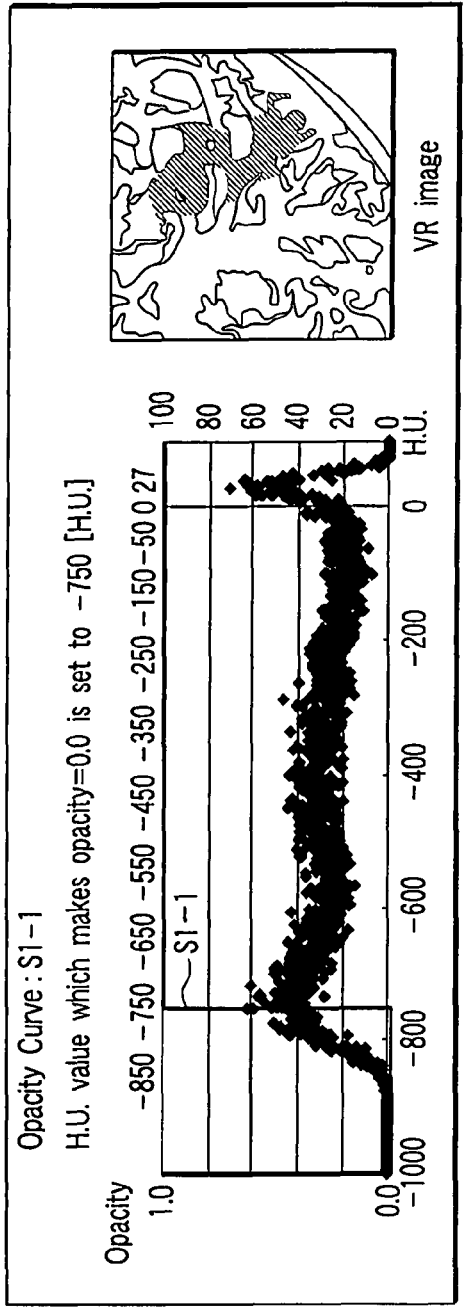
FIG. 27 is a graph showing an opacity curve with the gradient S1-1 and an H.U. value of −750 [H.U.] which makes opacity=0.0.
Figure 28:
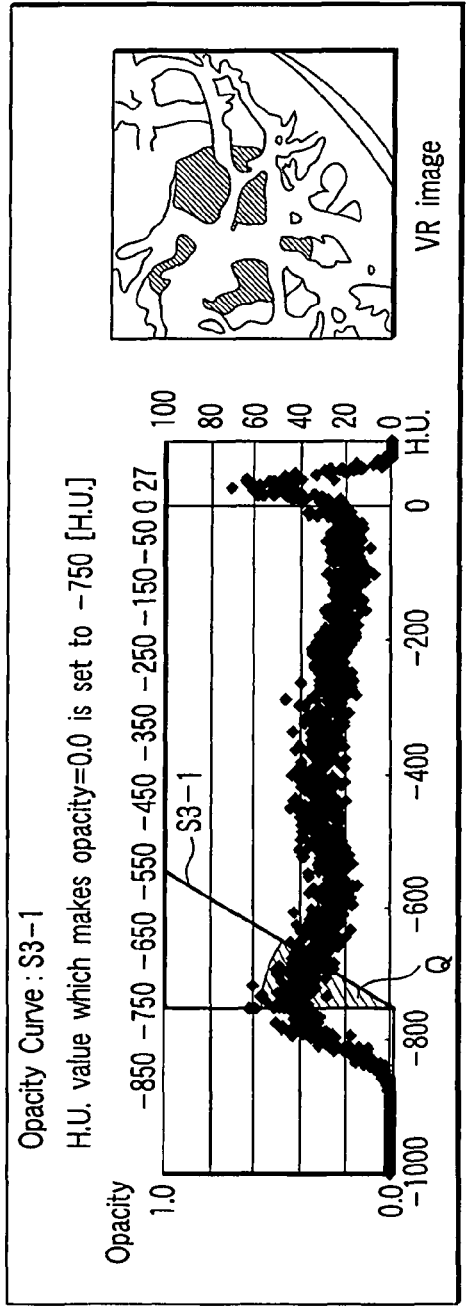
FIG. 28 is a graph showing an opacity curve with a gradient S3-1 and an H.U. value of −750 [H.U.] which makes opacity=0.0.
Figure 29:
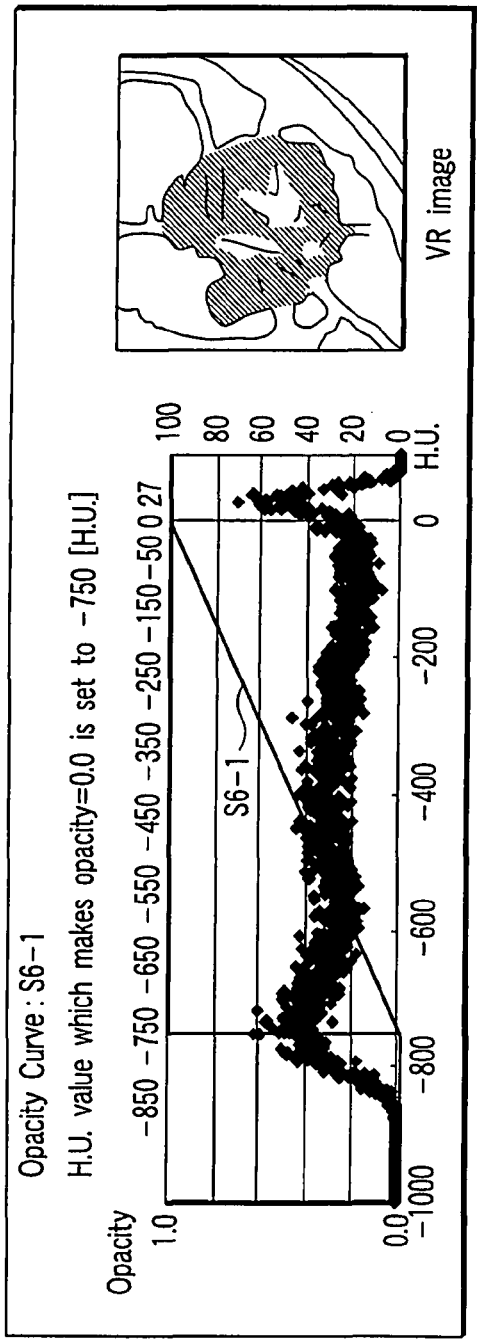
FIG. 29 is a graph showing an opacity curve with a gradient S6-1 and an H.U. value of −750 [H.U.] which makes opacity=0.0.

FIGS. 27 to 29 each show an opacity curve and the VR image generated by using the opacity curve in a case wherein the lower limit of the opacity is fixed to −750 [H.U.] and its gradient is changed in three steps (S1-1, S3-1, and S6-1). In the case in FIG. 27, many blood vessels and bronchi around the nodule are visualized, but the nodule itself is hidden. The image in FIG. 28 allows easy comprehension of the relationship between the nodule, its surrounding blood vessels, and the bronchi. Note that a region Q in FIG. 28 is a partial volume effect portion of peripheral bronchi or peripheral blood vessels. A VR image greatly changes depending on whether VR display includes this region. In the case in FIG. 29, the nodule is displayed in a form that is easy to observe by not displaying any surrounding structure of the nodule.

Figure 30:
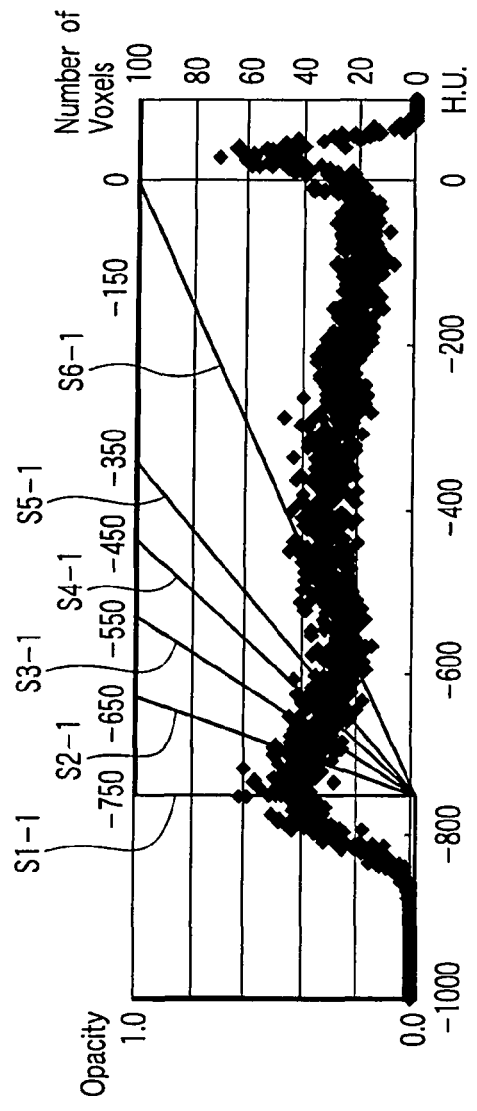
FIG. 30 is a graph showing an opacity curve obtained when the gradient is changed in six steps from S1-1 to S6-1.

For further reference, FIG. 30 shows how an opacity curve is displayed as the gradient is changed in six steps from S1-1 to S6-1.

(Effects)

According to the above arrangement, the following effects can be obtained.

In consideration of the fact that a lung field varies in the density of sponge-like tissue depending on an individual or a display region, this computer-aided imaging diagnostic processing apparatus can set an opacity curve which gives priority to a nodule candidate region or an extended nodule candidate region by generating a histogram concerning a volume of interest which includes a foreground region, and using the statistical analysis result on the histogram as an objective index. Therefore, an opacity curve can be properly set in accordance with a purpose, e.g., an observation target. This makes it possible to implement a computer-aided imaging diagnostic processing apparatus which can clearly visualize a nodule candidate region or an extended nodule candidate region.

In addition, this computer-aided imaging diagnostic processing apparatus automatically sets an opacity curve on the basis of a statistical analysis result on a histogram. This makes it possible to set VR parameters quickly and easily as compared with the prior art and to reduce the operation load on the user at the time of imaging diagnosis.

Furthermore, this computer-aided imaging diagnostic processing apparatus can change an automatically set opacity curve on a histogram concerning a volume of interest. Therefore, the user can quickly and accurately perform fine adjustment and change of an opacity curve.

Second Embodiment

Figure 31:
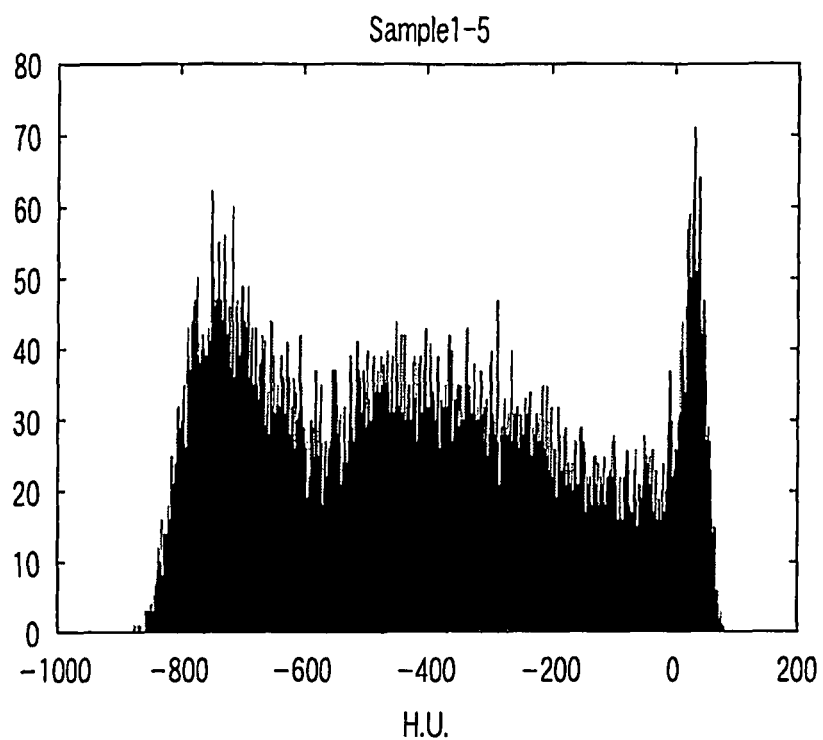
FIG. 31 is a graph for explaining control on the bin width of a histogram.
Figure 32:
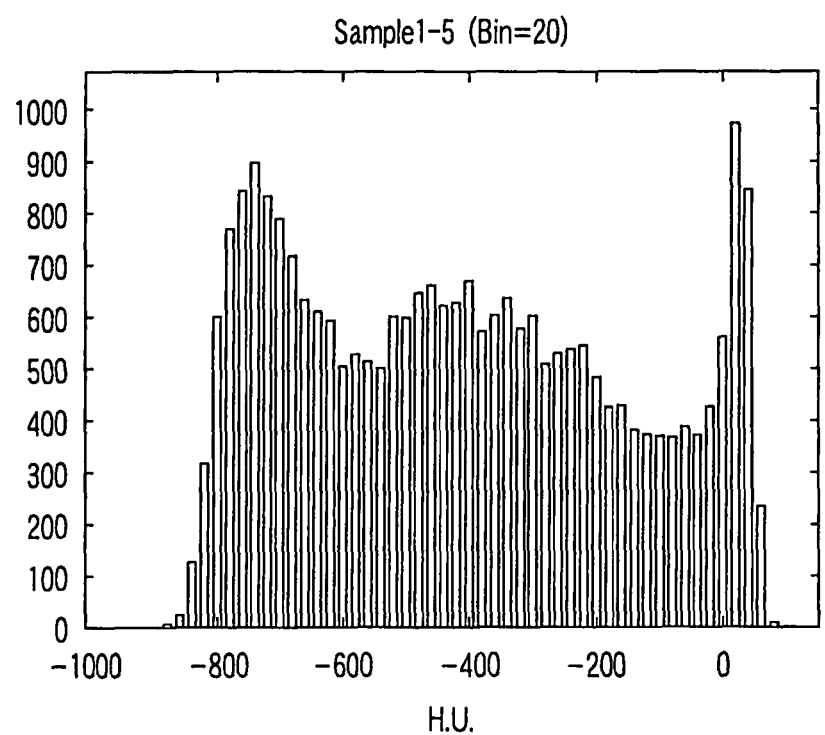
FIG. 32 is a graph for explaining control on the bin width of a histogram.

The second embodiment of the present invention will be described next. This embodiment can set the bin width of a histogram to an arbitrary value in accordance with operation by the operator through an operation unit 16 in VR parameter setting. In this case, the bin width is the width of each class on the abscissa of the histogram. For example, changing a bin width of 1 like that shown in FIG. 31 to a bin width of 20 will obtain a histogram like that shown in FIG. 32.

Note that a computer-aided imaging diagnostic processing apparatus according to this embodiment differs from that according to the first embodiment only in VR parameter setting processing corresponding to step S3 in FIG. 2.

Figure 33:
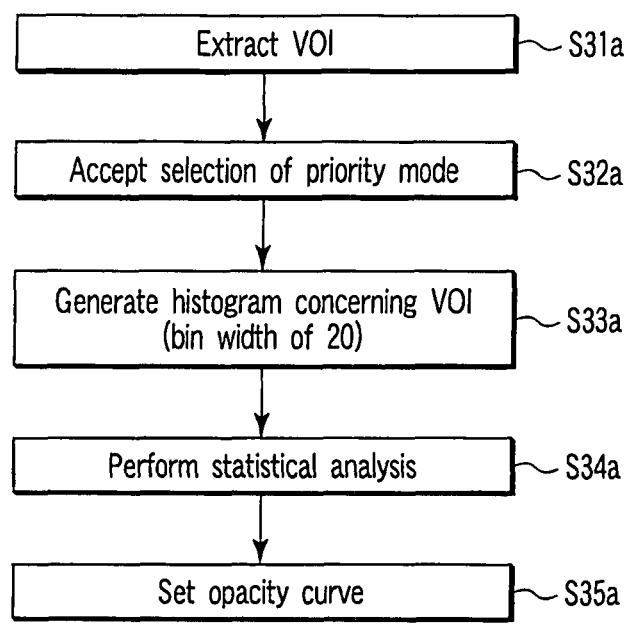
FIG. 33 is a flowchart showing a VR parameter setting processing procedure according to the second embodiment.

FIG. 33 is a flowchart showing a VR parameter setting processing procedure according to this embodiment. As shown in FIG. 33, first of all, a data analyzing unit 21 extracts a region including a foreground region as a VOI from a region segmented image generated in step S23 (step S31a). This VOI extraction processing is the same as that in step S31 in FIG. 5.

The data analyzing unit 21 then accepts the selection of the nodule candidate region priority mode or the extended nodule candidate region priority mode (step S32a).

The data analyzing unit 21 then generates a histogram with, for example, a bin width of 20 which is initially set, with respect to the extracted VOI (step S33a). Note that the setting of a bin width of 20 is merely an example, and the present invention is not limited to this. However, in VR parameter setting concerning a lung field, it is preferable to set a bin width to, for example, 10 or more and 20 or less.

The data analyzing unit 21 executes statistical analysis corresponding to the mode selected in step S33a by using an H.U. histogram concerning the generated VOI (step S34a).

When the nodule candidate region priority mode is selected, the data analyzing unit 21 calculates a Gaussian distribution function, its peak value, and the like by using a histogram like that shown in FIG. 34 with a bin width of 20 and an abscissa range from −1000 [H.U.] to 200 [H.U.]. When the extended nodule candidate region priority mode is selected, the data analyzing unit 21 calculates a Gaussian distribution function, its peak value, and the like by using a histogram like that shown in FIG. 35 with a bin width of 20 and an abscissa range from −1000 [H.U.] to −500 [H.U.].

The data analyzing unit 21 sets an opacity curve by determining an OWL and an OWW by using the statistical analysis result (step S35a). This opacity curve setting processing is the same as that in step S34 in FIG. 5.

According to the arrangement described above, this apparatus can set an opacity curve which gives priority to a nodule candidate region or an extended nodule candidate region by generating a histogram with a desired bin width which concerns a volume of interest and using the statistical analysis result on the histogram as an objective index. Therefore, setting the bin width to a proper value makes it possible to provide a highly reliable image with little influence from statistical analysis errors.

Third Embodiment

The third embodiment of the present invention will be described next. This embodiment stores opacity curves (i.e., OWL values and OWW values for the respective image types) for the respective image types obtained by the technique according to the first or second embodiment in correspondence with VR images, and allows the use of the opacity curves for the observation of the same region after the lapse of a predetermined period. An arrangement according to this embodiment is effective for a case wherein, for example, imaging diagnosis is to be performed on a patient's progress after operation or a temporal change in tumor is to be observed.

A computer-aided imaging diagnostic processing apparatus according to this embodiment differs from that of the first embodiment only in VR parameter setting processing corresponding to step S3 in FIG. 2.

In addition, the form of storing OWL values and OWW values for the respective image types is not specifically limited. Typically, there is available a form of storing them as additional information of VR images in a storage unit 18 or storing them in correspondence with IDs specifying VR images as files different from those of the VR images in the storage unit 18.

Figure 36:
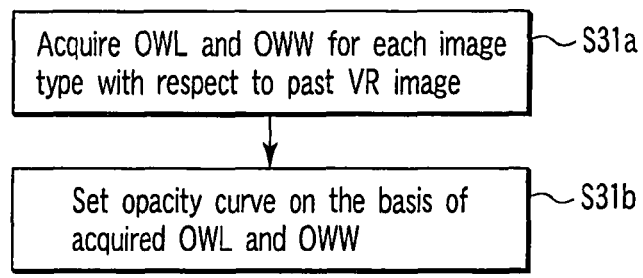
FIG. 36 is a flowchart showing a VR parameter setting processing procedure according to the third embodiment.

FIG. 36 is a flowchart showing a VR parameter setting processing procedure according to this embodiment. As shown in FIG. 36, first of all, a control unit 10 acquires VR images used for past imaging diagnosis and OWL values and OWW values for the respective image types used for the generation of the VR images on the basis of the ID of the patient, the examination ID, or the like (step S31b).

A data analyzing unit 21 sets an opacity curve used for the current imaging diagnosis by using the acquired OWL values and OWW values for the respective image types (step S31b).

Figure 37:
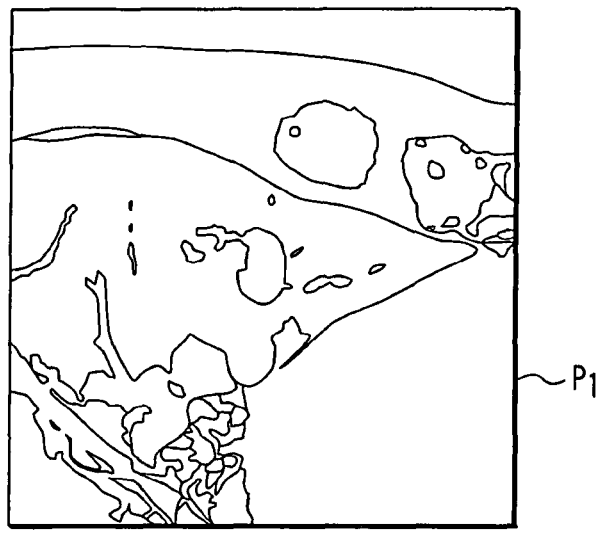
FIG. 37 is a view for explaining the effects of VR parameter setting processing according to the third embodiment.
Figure 38:
FIG. 38 is a view for explaining the effects of VR parameter setting processing according to the third embodiment.

FIG. 37 shows a VR image P1 concerning a nodule candidate region. FIG. 38 shows a VR image P2 generated by using the image data obtained by imaging the same nodule candidate region six months after the acquisition of the VR image P1 shown in FIG. 37 and the opacity curve set by using the technique according to this embodiment. Comparing and observing such images obtained with the same opacity curve at a given time interval allows easy visual checking of a temporal change in diagnosis region.

FIG. 37 shows the VR image P1 concerning the nodule candidate region. FIG. 38 shows the VR image P2 generated by using the image data obtained by imaging the same nodule candidate region six months after the acquisition of the VR image P1 shown in FIG. 37 and the opacity curve set by using the technique according to this embodiment. Comparing and observing such images obtained with the same opacity curve at a given time interval allow easy visual checking of a temporal change in diagnosis region when performing imaging diagnosis on the patient's progress after operation or observing a temporal change in tumor.

In addition, the arrangement according to this embodiment can quickly and simply reproduce the same parameter settings as those for a VR image based on which past diagnosis was made. This makes it possible to reduce artificial load at the time of imaging diagnosis and provide highly reliable diagnostic images.

Note that the present invention is not limited to the above embodiments, and constituent elements can be variously modified and embodied at the execution stage within the spirit and scope of the invention. The following are concrete modifications.

(1) Each function described in each embodiment can also be implemented by installing programs for executing the respective processes in a computer and unarchiving them in a memory. In this case, the programs which can cause the computer to execute the corresponding techniques can be distributed by being stored in recording media such as magnetic disks (floppy [registered trademark] disks, hard disks, and the like), optical disks (CD-ROMs, DVDs, and the like), and semiconductor memories.

(2) The above embodiments generate a histogram concerning the VOI included the only foreground region in a region segmented image. However, the present invention is not limited to this. For example, the present invention may generate a pulmonary mass and a blood vessel region from an image and generate a histogram concerning the extracted region. In addition, when an image includes the lobar fissure and pleura, the distribution of the histogram may become indistinct. In order to avoid such inconvenience, it suffices to generate a histogram after the removal of the lobar fissure and pleura from an image by region extraction processing.

In addition, various inventions can be formed by proper combinations of a plurality of constituent elements disclosed in the above embodiments. For example, several constituent elements may be omitted from the all the constituent elements in each embodiment. In addition, constituent elements of the different embodiments may be combined as needed.

What is claimed is:

1. A medical image processing apparatus which generates an image based on data acquired by using a medical imaging device, the apparatus comprising:
   a region specifying unit which specifies a nodule region in an image;
   a setting unit which sets a display type mode by selecting a nodule candidate region priority mode or an extended nodule candidate region priority mode;
   a parameter setting unit which executes statistical processing concerning an image in the nodule region and sets an opacity curve of the image based on a result of the statistical processing according to the set display type mode, wherein the statistical processing includes generating a histogram of an extracted volume of interest, and the opacity curve is set based on a first maximum H.U. value in a positive region on the histogram when the nodule candidate region priority mode is selected, and the opacity curve is set based on a second maximum H.U. value in a negative region on the histogram when the extended nodule candidate region priority mode is selected; and
   an image generating unit which generates a projection image based on the set opacity curve.

2. The apparatus according to claim 1, wherein the parameter setting unit selects a range of the histogram in response to the set display type mode and executes the statistical processing by using the selected range of the histogram.

3. The apparatus according to claim 2, wherein the parameter setting unit calculates the opacity curve by using the selected range of the histogram.

4. The apparatus according to claim 1, wherein the parameter setting unit sets the opacity curve based on a statistic calculated by statistical analysis using the histogram.

5. The apparatus according to claim 1, wherein
   the parameter setting unit executes, as the statistical processing, fitting based on a Gaussian function with reference to a predetermined position on the histogram and calculation of a statistic including an average value and a variance value, and sets the opacity curve in volume rendering processing based on the calculated statistic, and
   the image generating unit generates a three-dimensional image by executing volume rendering processing using the set opacity curve as the image generation processing.

6. The apparatus according to claim 1, wherein the setting unit sets the nodule candidate region priority mode for preferentially visualizing an abnormal candidate region or the extended nodule candidate region priority mode for preferentially visualizing the abnormal candidate region and a surrounding region thereof.

7. The apparatus according to claim 5, further comprising a designation unit which designates a shape of the opacity curve, wherein
the parameter setting unit sets the opacity curve having the designated shape.

8. The apparatus according to claim 3, further comprising a changing unit which changes the opacity curve set by the parameter setting unit, wherein
the image generating unit generates a three-dimensional image by executing volume rendering processing using the opacity curve changed by the changing unit.

9. The apparatus according to claim 3, further comprising a display unit which displays a generated three-dimensional image and the opacity curve used in the image generation processing.

10. The apparatus according to claim 3, further comprising a display unit which displays only an image corresponding to the extracted volume of interest.

11. The apparatus according to claim 3, further comprising a display unit which displays the histogram while superimposing characteristic information of opacity on the histogram.

12. The apparatus according to claim 11, wherein the parameter setting unit sets a width and position of a window, and acquires the opacity curve such that a value of opacity changes with a change in a voxel value in the window.

13. The apparatus according to claim 3, wherein the region setting unit extracts a region almost corresponding to lung blood vessel and a nodule as the nodule region.

14. The apparatus according to claim 3, wherein the parameter setting unit generates the histogram in accordance with one of an arbitrary bin width set by a user through the setting unit and a predetermined bin width which is initially set.

15. The apparatus according to claim 3, wherein the parameter setting unit generates the histogram in accordance with a bin width of 10 inclusive to 20 exclusive.

16. The apparatus according to claim 1, further comprising a storage unit which stores the opacity curve set by the parameter setting unit in correspondence with the image for which the statistical processing has been executed.

17. The apparatus according to claim 1, wherein the image generating unit generates the projection image by using an image different from the image for which the statistical processing has been executed and the opacity curve concerning the image for which the statistical processing has been executed.

18. A medical image processing method, comprising:
specifying a nodule region in an image acquired by using a medical imaging device;
setting a display type mode by selecting a nodule candidate region priority mode or an extended nodule candidate region priority mode;
executing statistical processing concerning an image in the nodule region according to the set display type mode and setting an opacity curve of the image based on a result of the statistical processing, wherein the statistical processing includes generating a histogram of an extracted volume of interest, and the opacity curve is set based on a first maximum H.U. value in a positive region on the histogram when the nodule candidate region priority mode is selected, and the opacity curve is set based on a second maximum H.U. value in a negative region on the histogram when the extended nodule candidate region priority mode is selected; and
generating a projection image based on the set opacity curve.

* * * * *